(12) United States Patent
Ookubo et al.

(10) Patent No.: US 9,885,667 B2
(45) Date of Patent: Feb. 6, 2018

(54) CAN BODY INSPECTION APPARATUS AND METHOD

(71) Applicant: Toyo Seikan Group Holdings, Ltd., Tokyo (JP)

(72) Inventors: Wataru Ookubo, Yokohama (JP); Masayuki Nakamura, Yokohama (JP)

(73) Assignee: TOYO SEIKAN GROUP HOLDINGS, LTD., Tokyo (JP)

(*) Notice: Subject to any disclaimer, the term of this patent is extended or adjusted under 35 U.S.C. 154(b) by 128 days.

(21) Appl. No.: 14/442,250

(22) PCT Filed: Oct. 24, 2013

(86) PCT No.: PCT/JP2013/078787
§ 371 (c)(1),
(2) Date: May 12, 2015

(87) PCT Pub. No.: WO2014/077099
PCT Pub. Date: May 22, 2014

(65) Prior Publication Data
US 2016/0274034 A1    Sep. 22, 2016

(30) Foreign Application Priority Data

Nov. 13, 2012  (JP) .................................. 2012-249202

(51) Int. Cl.
*G01N 21/90* (2006.01)
*G01N 21/894* (2006.01)
(Continued)

(52) U.S. Cl.
CPC ......... *G01N 21/909* (2013.01); *G01N 21/894* (2013.01); *G01N 21/90* (2013.01);
(Continued)

(58) Field of Classification Search
USPC .... 356/237.1–241.6, 242.1–243.8, 426–431, 356/600–640
See application file for complete search history.

(56) References Cited

U.S. PATENT DOCUMENTS 3,894,806 A * 7/1975 Remy ................... B07C 5/3404
                                                                 250/223 B
3,941,686 A * 3/1976 Juvinall .................. B07C 5/122
                                                                 209/523

(Continued)

FOREIGN PATENT DOCUMENTS

JP    H01-260585    10/1989
JP    H04-64042     2/1992

(Continued)

OTHER PUBLICATIONS

International Search Report for International Application No. PCT/JP2013/078787 dated Dec. 3, 2013.

(Continued)

*Primary Examiner* — Kara E Geisel
*Assistant Examiner* — Jarreaus C Underwood
(74) *Attorney, Agent, or Firm* — Kratz, Quintos & Hanson, LLP

(57) ABSTRACT

A can body inspection apparatus which prevents a drop in resistance to noise while enabling high speed inspection is provided. It is comprised of a light source control means (21, 22) for turning on the light source unit a predetermined number of times of two times or more at predetermined timings at which light can be taken in by the light-detection unit through the open end face of the can body W which is moving along the path of conveyance W, a detection signal integrating means 23 for integrating signal values based on the detection signal which is output from the light-detection unit 15 due to on operations of the light source unit 10, and a condition judging means 24 for using an integrated value (Continued)

which is obtained by the detection signal integrating means 23 as the basis to judge the condition of the can body.

15 Claims, 4 Drawing Sheets

(51) Int. Cl.
  *G01N 21/952* (2006.01)
  *G01N 21/84* (2006.01)
(52) U.S. Cl.
  CPC ... *G01N 21/952* (2013.01); *G01N 2021/8455* (2013.01); *G01N 2201/062* (2013.01); *G01N 2201/068* (2013.01)

(56) References Cited

U.S. PATENT DOCUMENTS

| | | | | |
|---|---|---|---|---|
| 4,074,809 A | * | 2/1978 | McMillin | B07C 5/3404 209/588 |
| 4,086,497 A | * | 4/1978 | Murray | G01M 3/38 250/223 R |
| 4,428,674 A | * | 1/1984 | Giebel | G01N 21/90 250/223 B |
| 4,680,463 A | * | 7/1987 | Lutgendorf | B07C 5/126 250/223 B |
| 4,682,023 A | * | 7/1987 | Yoshida | G01N 21/9054 250/223 B |
| 4,915,237 A | * | 4/1990 | Chang | B07C 5/122 198/406 |
| 4,924,107 A | * | 5/1990 | Tucker | G01N 21/909 250/559.08 |
| 4,983,822 A | * | 1/1991 | Fukuchi | G01N 21/90 250/223 B |
| 5,095,204 A | * | 3/1992 | Novini | G01N 21/9045 250/223 B |
| 5,699,152 A | * | 12/1997 | Fedor | G01N 21/909 356/240.1 |
| 6,226,081 B1 | * | 5/2001 | Fantone | G01F 23/292 250/223 B |
| 6,272,437 B1 | * | 8/2001 | Woods | G01N 23/04 700/110 |
| 6,473,169 B1 | * | 10/2002 | Dawley | G01M 3/3263 250/223 B |
| 6,519,356 B1 | * | 2/2003 | Hooker | G01N 21/9036 209/524 |
| 6,781,688 B2 | * | 8/2004 | Kren | G01N 21/9501 356/237.1 |
| 7,545,972 B2 | * | 6/2009 | Itoh | G06K 9/00 382/142 |

FOREIGN PATENT DOCUMENTS

| | | |
|---|---|---|
| JP | H06-109661 | 4/1994 |
| JP | 2004-294369 A | 10/2004 |
| JP | 2004-294391 A1 | 10/2004 |
| JP | 2009-025131 A | 2/2009 |
| JP | 4322530 B2 | 9/2009 |

OTHER PUBLICATIONS

European Application No. 13855059: Extended European Search Report dated Jun. 2, 2016.

* cited by examiner

CAN BODY INSPECTION APPARATUS AND METHOD

TECHNICAL FIELD

The present invention relates to a can body inspection apparatus and method for inspecting for the presence of any pinhole or crack etc. in a can body.

BACKGROUND ART

In the past, a can pinhole inspection method (see PLT 1) and a can body pinhole inspection apparatus (see PLT 2) have been proposed. In such a can pinhole inspection method or inspection apparatus, when the conveyed can body passes through an inspection area including a predetermined position where a sensor is set, light is irradiated from plural sources of light, and the amount of light which leaks through an opening part of the can body is measured by the sensor to detect a pinhole in the can body. Specifically, while a can body passes through the inspection area, the light source is switched on, off, and on in state. It is judged that the can body is free of pinholes when all of the three measurement values among the three measurement values of the amounts of light by the sensor in the different states are the threshold value or less, it is judged that the can body has a pinhole when two of the measurement values exceed the threshold value, and it is judged that there is leakage of light or another abnormality in inspection when all of the three measurement values exceed the threshold value.

According to such a can body pinhole inspection method, it is judged that there is a pinhole in the can body only when two of the measurement values among the three measurement values exceed the threshold value, so it becomes possible to prevent mistaken detection of pinholes and perform more accurate inspection.

CITATIONS LIST

Patent Literature

PLT 1: Japanese Patent No. 4322530B
PLT 2: Japanese Patent Publication No. 06-109661A

SUMMARY OF INVENTION

Technical Problem

In this regard, in such can body inspection, high speed inspection is being demanded. For this reason, the time during which a can body passes through the inspection area is tending to become shorter. Along with this, the on time and off time of the light source have become shorter. For this reason, the absolute value of the amount of light which can measured by a sensor during one on state of the power supply is tending to become lower. In view of this situation, it is necessary to set the threshold value which is used as a reference for judging suitability relatively low.

However, if lowering the threshold value, the resistance to noise falls and the possibility of mistaken detection ends up becoming higher.

The present invention was made in consideration of such a situation and provides a can body inspection apparatus and method which prevent a drop in resistance to noise while enabling high speed inspection.

Solution to Problem

The can body inspection apparatus according to the present invention provides a can body inspection apparatus which comprises a conveyance mechanism which conveys a can body with an open end, a light source unit which emits light to a can body which moves along the inside of a path of conveyance, and a light-detection unit which is arranged so as to face the open end face of the can body at a predetermined position inside the path of conveyance, which takes in the light which is leaked through the open end face to the inside of the can body which is irradiated by the light from the light source unit which is turned on, and which outputs a detection signal which corresponds to the amount of light which is taken in and which uses the detection signal from the light-detection unit as the basis to inspect the can body, the can body inspection apparatus comprising light source control means for turning on the light source unit a predetermined number of times of two times or more at predetermined timings at which light can be taken in by the light-detection unit through the open end face of the can body which is moving along the path of conveyance, detection signal integrating means for integrating signal values based on the detection signal which is output from the light-detection unit due to on operations of the light source unit, and condition judging means for judging condition of the can body based on an integrated value which is obtained by the detection signal integrating means.

Due to such a configuration, the light source unit is made to turn on a predetermined number of times of two times or more at predetermined timings at which light can be taken in by the light-detection unit through the open end face of the can body which is moving along the path of conveyance, signal values based on the detection signal which is output from the light-detection unit due to on operations of the light source unit are integrated, and the integrated value is used as the basis to judge the condition of the can body.

In the can body inspection apparatus according to the present invention, the detection signal integrating means can be configured to integrate, as the signal values, peak level values of the detection signal which is output from the detection unit due to on operations of the light source unit.

Further, in the can body inspection apparatus according to the present invention, the judging means can judge the condition of the can body based on whether the integrated value which is obtained by the detection signal integrating means is larger than a predetermined threshold value.

Further, in the can body inspection apparatus according to the present invention, the light source control means can turn the light source unit on at least at two timings of a timing right before a reference timing at which the open end face of the can body directly faces the light-detection unit and a timing right after the reference timing.

Furthermore, in the can body inspection apparatus according to the present invention, the time period between the reference timing and the timing right before when the light source unit is turned on and the time period from the reference timing to the timing right after when the light source unit is turned on can be set the same.

Further, in the can body inspection apparatus according to the present invention, the conveyance mechanism can convey the can body without allowing it to rotate in an area at which light can be taken in by the light-detection unit through the open end face of the moving can body.

Furthermore, the can body inspection apparatus according to the present invention can further comprise light source condition judging means for using the presence of a current which flows through the light source unit at a timing for supplying power from a power supply to turn on the light source unit as the basis to judge the condition of the light source unit.

The can body inspection method according to the present invention provides a can body inspection method which uses a can body inspection apparatus which comprises a conveyance mechanism which conveys a can body with an open end, a light source unit which irradiates light to a can body which moves along the inside a path of conveyance, and a light-detection unit which is arranged so as to face the open end face of the can body at a predetermined position inside the path of conveyance, which takes in the light which is leaked through the open end face to the inside of the can body which is irradiated by the light from the light source unit which is turned on, and which outputs a detection signal which corresponds to the amount of light which is taken in and which uses the detection signal from the light-detection unit as the basis to inspect the can body, the can body inspection method comprising a lighting step of turning on the light source unit a predetermined number of times of two times or more at predetermined timings at which light can be taken in by the light-detection unit through the open end face of the can body which is moving along the path of conveyance a detection signal integrating step of integrating signal values based on the detection signal which is output from the light-detection unit due to on operations of the light source unit, and a condition judging step of judging condition of the can body based on an integrated value which is obtained by said detection signal integrating step.

In the can body inspection method according to the present invention, the detection signal integrating step can integrate, as the signal values, peak level values of the detection signal which is output from the detection unit due to on operations of the light source unit.

Advantageous Effects of Invention

According to the can body inspection apparatus and method according to the present invention, even if the level of the detection signal as a whole from the light-detection unit at the time of one on operation of the light source unit is low due to the high speed conveyance of the can body, the light source unit is made to turn on by a predetermined number of times of two times or more and the integrated value of the signal values based on the detection signal which is output from the light-detection unit is used as the basis to judge the condition of the can body, so the integrated value of the signal values based on the detection signal forming the foundation for judgment of the can body condition can become larger than the noise. Therefore, it is possible to prevent a drop in resistance to noise while enabling high speed inspection.

DESCRIPTION OF EMBODIMENTS

Figure 1:
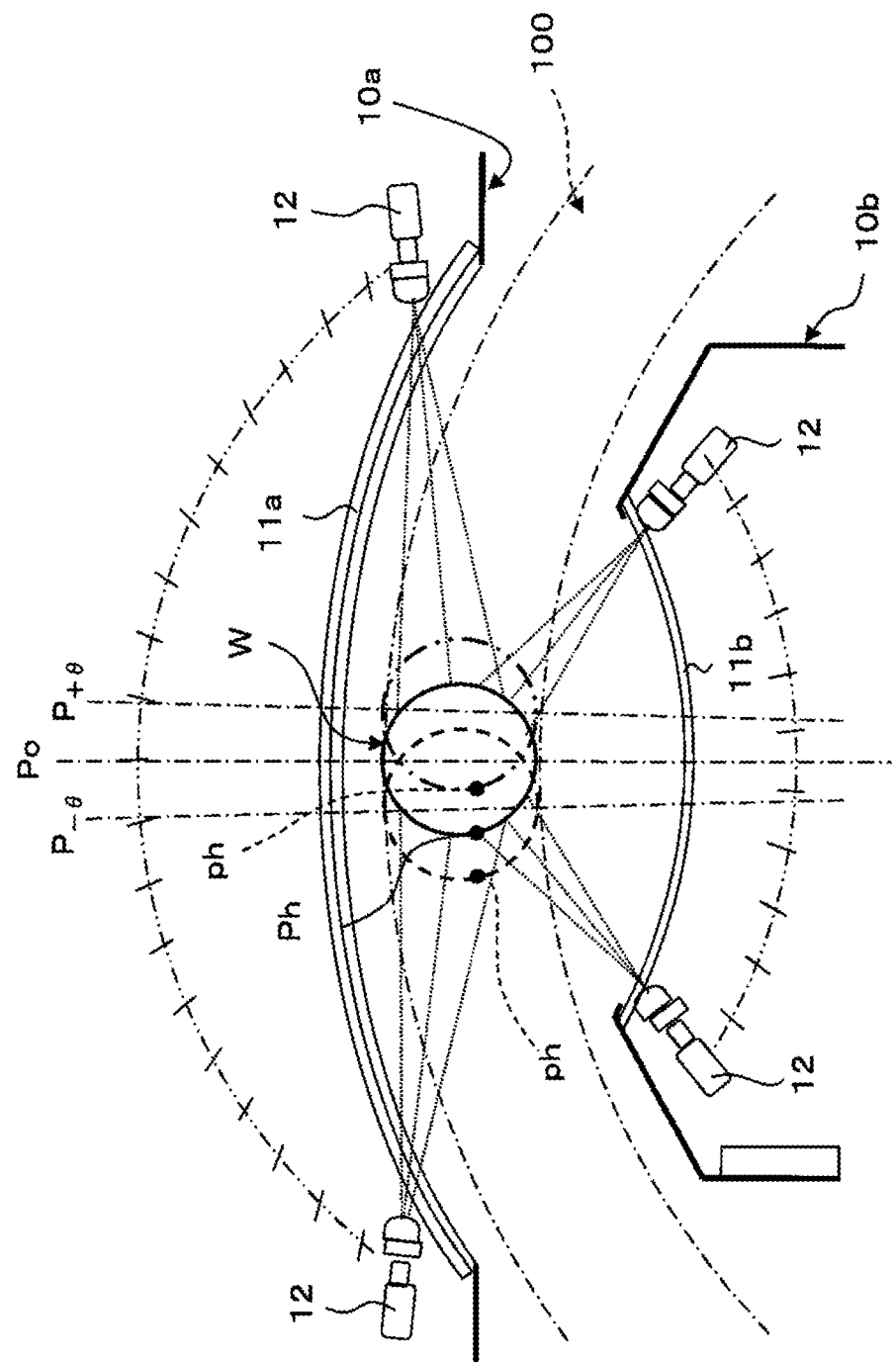
FIG. 1 is a front view which shows the structure of a can body inspection apparatus according to an embodiment of the present invention as seen from the front.
Figure 2:
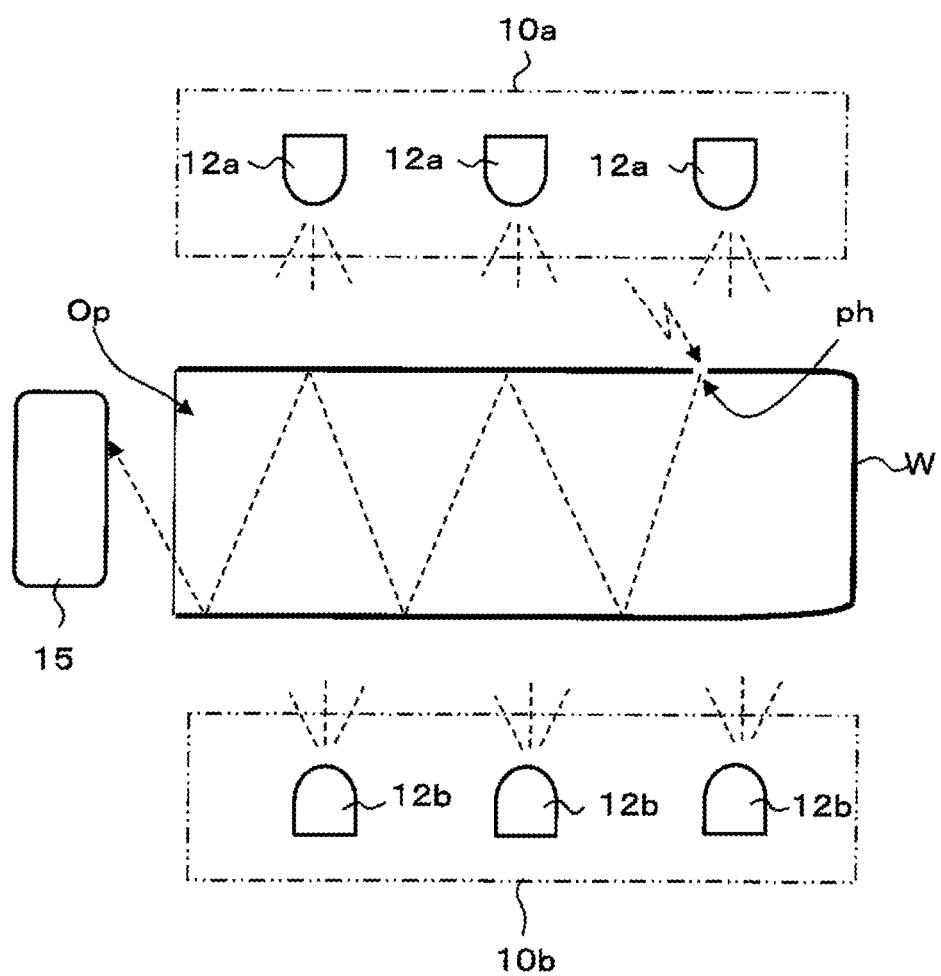
FIG. 2 is a view of principal parts of a mechanical system which is shown in FIG. 1 (light source unit and light-detection unit) as seen from the side.

A mechanical system in a can body inspection apparatus according to one embodiment of the present invention is substantially the same in basic configuration as the inspection apparatus which is disclosed in Japanese Patent Publication No. 6-109661A (PLT 2) and is configured such as shown in FIG. 1 and FIG. 2. FIG. 1 is a view of the mechanical system as seen from the front, while FIG. 2 is a view of principal parts of the mechanical system (light source unit and light-detection unit) as seen from the side. Note that, the can body to be inspected is a beverage can body which is made of a metal, for example, is made of aluminum.

In FIG. 1 and FIG. 2, can bodies W with opening parts Op at single ends are held in a plurality of pockets which are formed at the peripheral part of a disk shaped turret (conveyance mechanism: not shown). By rotation of the turret, the can bodies W are conveyed along the inside of an arc-shaped path of conveyance 100 without being rotated. An upper side light source unit 10a and a lower side light source unit 10b are arranged facing each other across the path of conveyance 100. At the upper side light source unit 10a, a plurality of LEDs (light emitting diodes) 12 which are held in the housing are arranged at equal intervals along a surface which is curved in a direction the same as the curved direction of the arc-shaped path of conveyance 100. At the lower side light source unit 100b, a plurality of LEDs 12 which are held in the housing are arranged at equal intervals along a surface which is curved in a reverse direction to the curved direction of the arc-shaped path of conveyance 100. The housing of the upper side light source unit 10a is provided with a transparent window 11a which faces the path of conveyance 100. Light from the plurality of LEDs 12 in the housing passes through the transparent window 11a to be irradiated on a can body W in the path of conveyance 100. The housing of the lower side light source unit 10b is provided with a transparent window 11b facing the path of conveyance 100. Light from the plurality of LEDs 12 in the housing passes through the transparent window 11b to be irradiated on a can body W in the path of conveyance 100.

The LEDs 12 of the upper side light source unit 10a are set in directions of radiation of light so as to irradiate a can body W which is at a predetermined origin position Po in the path of conveyance 100 from the upper side direction. Further, the LEDs 12 of the lower side light source unit 10b are set in directions of radiation of light so as to irradiate a can body W which is at the origin position Po from the lower side direction.

A light-detection unit 15 (for example, a photomultiplier tube) is arranged so as to directly face an open end face which is formed at the opening part Op of the can body W at the origin position Po of the path of conveyance 100 (in particular, see FIG. 2). The light-detection unit 15, when there is a pinhole ph in the can body W which is irradiated by light from the above-mentioned upper side light source unit 10a and lower side light source unit 10b, takes in the light which leaks through the opening part Op (open end face) to the inside of the can body W and outputs a detection signal which corresponds to the amount of light which is taken in. Note that, while not shown, between the can body W at the origin position Po which is held at the turret and the light-detection unit 15, to prevent outside light from striking the light-detection unit 15, a light blocking mechanism is provided which is comprised of a sliding ring plate which has a through hole which faces the opening part Op of the can body W which is attached to the turret and a sealing member which surrounds an observation window of the light-detection unit 15 and is press bonded to the sliding ring plate. The can body W is made to advance by a bottom chuck in the axial direction so as to press the opening part Op against the sliding ring plate in at least the section passing in front of the light-detection unit 15.

Figure 3:
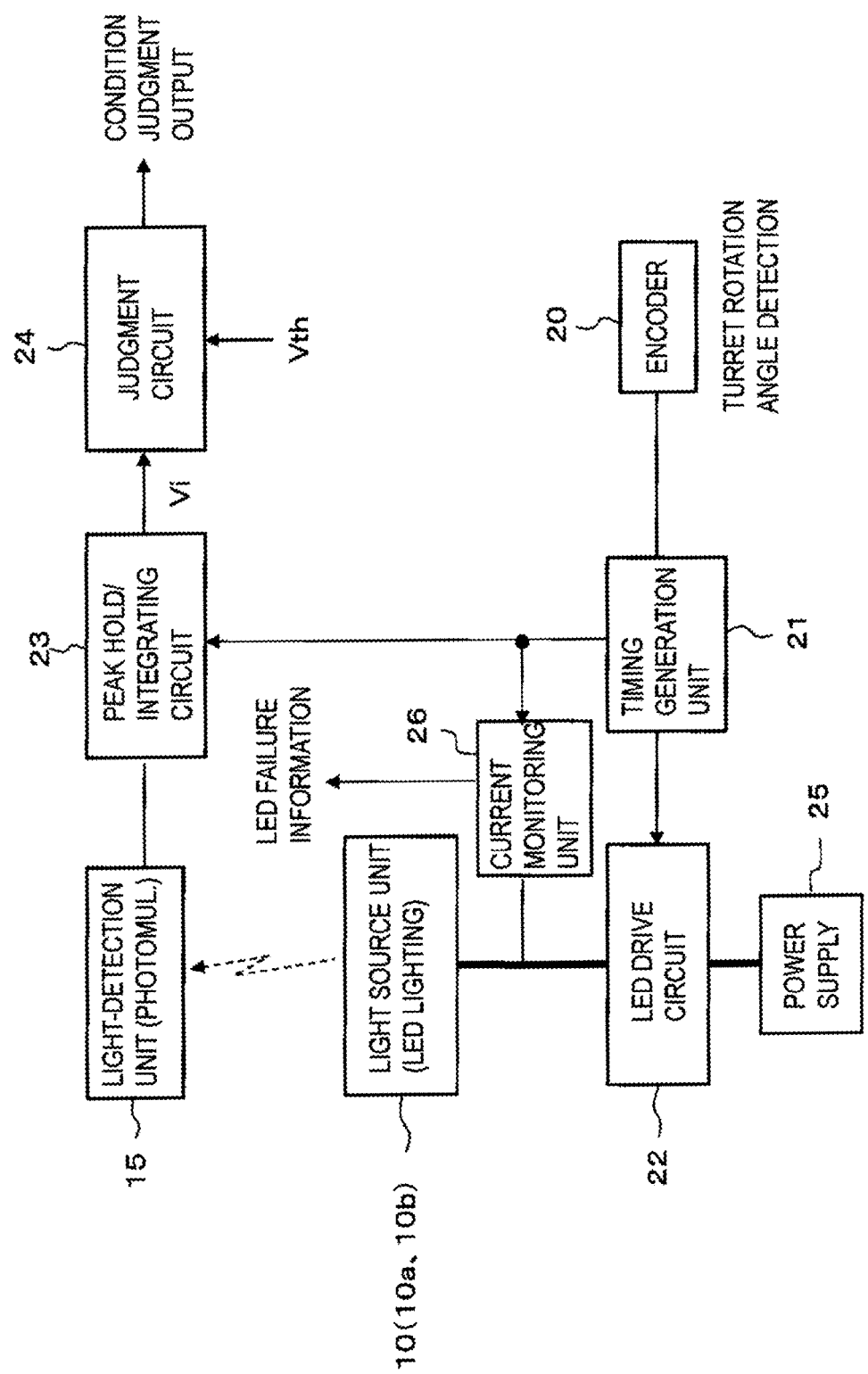
FIG. 3 is a block diagram which shows the configuration of a can body inspection apparatus according to an embodiment of the present invention.

The can body inspection apparatus according to one embodiment of the present invention is configured as shown in FIG. 3.

In FIG. 3, this can body inspection apparatus comprises an encoder 20 which detects a rotation angle of the turret which conveys the can body W and outputs position information which expresses the position of the can body W in the path of conveyance 100 and a timing generation unit 21 which uses the position information from the encoder 20 as the basis to output timing signals. Further, the can body inspection apparatus has a power supply 25, an LED drive circuit 22 which drives the LEDs 12 of the light source unit 10 ("light source unit 10" is the overall term for the upper side light source unit 10a and lower side light source unit 10b which are shown in FIG. 1 and FIG. 2, same below) by power from the power supply 25, and a current monitoring unit 26 which monitors the current which flows through the LEDs 12 of the light source unit 10.

The timing generation unit 21 (light source control means) generates and outputs light radiation timing signals which express light radiation timings of the LEDs 12 so as to make the LEDs 12 of the light source unit 10 emit light at predetermined timings at which light passing through the open end face (opening part Op) of a can body W which moves along the inside of the path of conveyance can be taken in by the light-detection unit 15 based on position information from the encoder 20. The light radiation timings specifically are timings when rotation of the turret causes a can body W to move in a zone where the through hole of the sliding ring plate of the turret and the observation window of the light-detection unit 15 passing through the sealing member overlap by a certain amount or more. The timing generation unit 21 outputs a first light emitting timing signal when the can body W is at a position P-θ (see FIG. 1) at the upstream side from the origin position Po by exactly the amount of the rotation angle θ of the turret (for example, 2.5 degrees) and outputs a second light emitting timing signal when the can body W passes the origin position Po and is at a position P+θ (see FIG. 1) at the downstream side from the origin position Po by exactly the amount of the rotation angle θ of the turret (for example, +2.5 degrees). The LED drive circuit 22 (light source control means) makes the LEDs 12 of the light source unit 10 emit light (makes the light source unit 10 turn on) for exactly predetermined times (for example, 1.5 msec) from the rising edges of the first light emitting timing signal and second light emitting timing signal from the timing generation unit 21. Further, the current monitoring unit 26 (light source condition judging means) judges if the currents which flow through the LEDs 12 of the light source unit 10 at the predetermined times (for example, 1.5 msec) from the rising edges of the first light emitting timing signal and second light emitting timing signal from the timing generation unit 21 are normal and, when abnormal, outputs LED failure information.

The can body inspection apparatus further has a peak hold/integrating circuit 23 and judgment circuit 24. The peak hold/integrating circuit 23 (detection signal integrating means) holds the peak level values Vp1, Vp2 (signal values) of the detection signal which is output from the light-detection unit 15 for predetermined times (for example 2.5 msec) longer than the light radiation times of the LEDs 12 (for example, 1.5 msec) from the rising edges of the first light emitting timing signal (corresponding to position P-θ in FIG. 1) and second light emitting timing signal (corresponding to position P+θ in FIG. 1) from the timing generation unit 21, integrates these peak level values Vp1 and Vp2 of the detection signal, and outputs the integrated value Vi (=Vp1+Vp2). The judgment circuit 24 (condition judging means) judges if the integrated value Vi from the peak hold/integrating circuit 23 is larger than a predetermined threshold value Vth. Further, the judgment circuit 24 outputs a condition judgment signal which indicates that the can body W has a pinhole or fracture and is defective when the integrated value Vi is larger than the threshold value Vth and which indicates that the can body W does not have a pinhole or fracture and is good when the integrated value Vi is the threshold value Vth or less.

Figure 4:
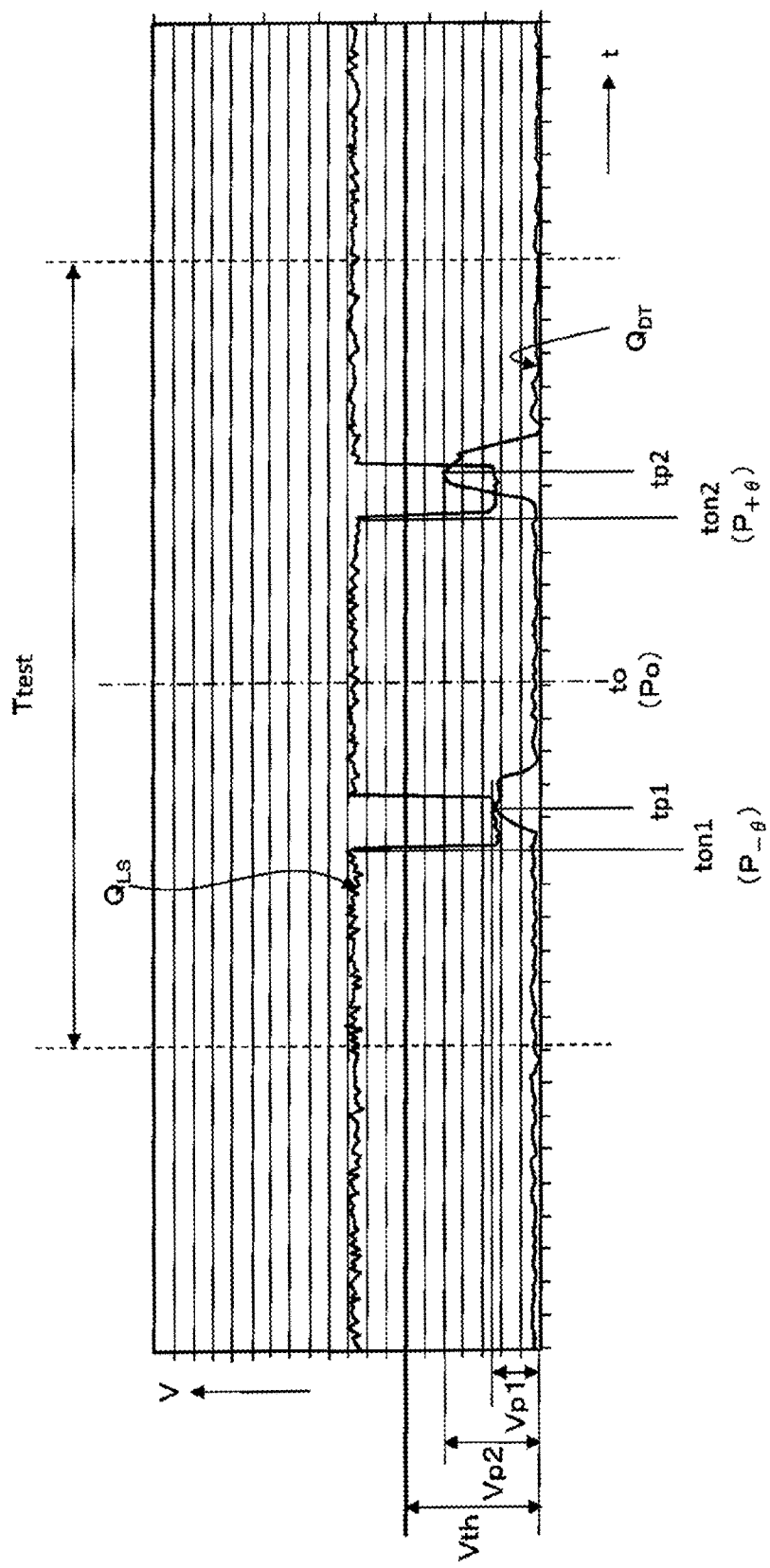
FIG. 4 is a signal waveform diagram of the waveform of feed of power to the light source unit in the can body inspection apparatus which is shown in FIG. 1 and FIG. 3 and the waveform of the detection signal from the light-detection unit.

In the above-mentioned can body inspection apparatus, in synchronization with the first light emitting timing signal which is output from the timing generation unit 21, for example, as shown in the signal waveform QLS of FIG. 4, the LEDs 12 of the light source unit 10 emit light for exactly a predetermined time (for example 1.5 msec) from the first timing ton1 where the can body W which moves along the inside of the path of conveyance 100 reaches the position P-θ right before the origin position Po (see FIG. 1). Further, in synchronization with the second light emitting timing signal which is output from the timing generation unit 21 after the first light emitting timing signal, the LEDs 12 of the light source unit 10 emit light for exactly a predetermined time (for example 1.5 msec) from the second timing ton2 where the can body W passes the origin position Po (corresponding to timing to) and reaches the position P+θ right after the origin position Po (see FIG. 1).

Here, for example, as shown in FIG. 1, when there is a pinhole ph at a position of the can body W where the can body W becomes truly horizontal at the downstream side when at the origin position Po (position of 90 degrees), as shown by the signal waveform QDT of FIG. 4, the level of the detection signal from the light-detection unit 15 rises due to the light which leaks to the inside from the pinhole ph of the can body W at the position P-θ (see FIG. 1) which is irradiated by light from the light source unit 10 which turns on for a predetermined time (for example, 1.5 msec) from the first timing ton1. Further, the level of the detection signal from the light-detection unit 15 rises due to the light which leaks to the inside from the pinhole ph of the can body W at the position P+θ (see FIG. 1) which is irradiated by light from the light source unit 10 which turns on for a predetermined time (for example, 1.5 msec) from the second timing ton2.

Note that, when the can body W is at a position P-θ right before the origin position Po, the pinhole ph is relatively far from the LEDs 12 of the upper side light source unit 10a which irradiates the pinhole ph. Further, the pinhole ph is irradiated at a slant. As opposed to this, when the can body W is at a position P+θ right after the origin position Po, the pinhole ph is relatively close to the LEDs of the upper side light source unit 10a which irradiates the pinhole ph. Further, the pinhole ph is irradiated from approximately the front. For this reason, as shown by the signal waveform QDT of FIG. 4, the overall level of the detection signal which is output from the light-detection unit 15 due to the light from the light source unit 10 which turns on for a predetermined time (for example, 1.5 msec) from the first timing ton1 is lower than the overall level of the detection signal which is output from the light-detection unit 15 due to the light from the light source unit 10 which turns on for a predetermined time (for example, 1.5 msec) from the second timing tong.

In the above-mentioned situation, the peak hold/integrating circuit 23 successively holds peak level values of the detection signal from the light-detection unit 15 over a predetermined time (for example, 2.5 msec) longer than an on time of the light source unit 10 (light radiation times of LEDs 12) from the rising edge of the first light radiation timing signal (corresponding to first timing ton1). Due to this, as shown by the signal waveform QDT of FIG. 4, a peak level value Vp1 at for example the timing tp1 of a detection signal from the light-detection unit 15 which rises due to the light from the light source unit 10 which turns on at the first timing Ton1 is obtained. Further, the peak hold/integrating circuit 23 successively holds peak level values of the detection signal from the light-detection unit 15 over a predetermined time (for example, 2.5 msec) from the rising edge of the second light emitting timing signal (corresponding to second timing tong). Due to this, as shown by the signal waveform QDT of FIG. 4, a peak level value Vp2 at for example the timing tp2 of a detection signal from the light-detection unit 15 which rises due to the light from the light source unit 10 which turns on at the second timing Ton2 is obtained. The peak level value Vp1 becomes lower than the peak level value Vp2. As a method for dealing with the detection level becoming lower depending on the position of formation of the pinhole, for example, it may be considered to inspect the can body while making it rotate, but increasing the speed of inspection is liable to become difficult and mechanical vibration is liable to cause an increase in detection error.

The peak hold/integrating circuit 23 integrates the two obtained peak level values Vp1 and Vp2 and outputs the integrated value Vi, while the judgment circuit 24 compares this integrated value Vi and a predetermined threshold value Vth and, since the integrated value Vi becomes larger than the threshold value Vt, judges that there is a pinhole ph and outputs a judgment signal which indicates a defect. Note that, it is also possible to use the above judgment signal as the basis to remove a can body W which has been judged as defective from the path of conveyance 100 (turret).

In the above-mentioned can body inspection apparatus, even if the first on time of the light source unit 10 (for example, 1.5 msec) becomes shorter due to high speed conveyance of the can body W and the level of the detection signal as a whole from the light-detection unit 15 due to the light which is emitted from the light source unit 10 becomes low (see signal waveform QDT of FIG. 4), the light source unit 10 is turned on two times (first timing ton1 and second light emitting timing tong) and the integrated value Vi of the peak level values Vp1 and Vp2 (signal values) of the detection signal which is output from the light-detection unit due to the on operations is used as the basis to judge the condition of the can body, so the integrated value Vi of the peak level values Vp1 and Vp2 of the detection signal which forms the foundation for judgment of the condition of the can body can become larger than the noise. Therefore, even if setting the threshold value Vth for judgment of condition relatively high, for example, as shown in FIG. 4, even with a threshold value Vth which is higher than the individual peak level values Vp1 and Vp2, the integrated value Vi exceeds the threshold value Vth, so it can be precisely judged if the can body W being inspected is a can body with a pinhole or fracture. That is, it becomes possible to prevent a drop in resistance to noise while enabling high speed inspection of a can body W.

Further, as explained above, the current monitoring unit 26 judges if the currents which flow through the LEDs 12 of the light source unit 10 at the predetermined times (for example, 1.5 msec) from the rising edges of the first light emitting timing signal and the second light emitting timing signal are normal and, when abnormal, outputs LED failure information. Further, when the LED failure information from the current monitoring unit 26 is output, that LED failure information may be used as the basis to make the operation of the can body inspection apparatus stop, display a warning message on the display part, or perform other processing.

Note that, in the above-mentioned can body inspection apparatus, the light source unit 10 was turned on two times at the first timing ton1 and second timing tong at which light can be taken in by the light-detection unit 15 through the open end face of the can body W which moves along the path of conveyance 100, but it may also be made to emit light three times or more. In this case, the condition of the can body W is judged based on a comparison between the integrated value of the peak level values of the detection signal which is output from the light-detection unit 15 due to the radiation of light by the light source unit 10 three times or more and the threshold value th.

Further, the timings for making the light source unit 10 emit light are not particularly limited so long as timings at which light can be taken in by the light-detection unit 15 through an open end face of a can body W which moves along the path of conveyance 100.

In the above-mentioned can body inspection apparatus, the peak level values of the detection signal which is output from the light-detection unit 15 due to light radiation from the light source unit 10 are integrated as signal values of the detection signal, but the invention is not limited to this. The integrated value or average value of the detection signal which is output from the light-detection unit 15 due to light radiation from the light source unit 10 in a predetermined time, the level values after a predetermined time from the timings of on operations of the light source unit 10, or some other signal values based on the detection signal can be used.

INDUSTRIAL APPLICABILITY

As explained above, the can body inspection apparatus and method according to the present invention have the effect of preventing a drop in resistance to noise while enabling high speed inspection of the presence of pinholes etc. in a can body. This is useful as a can body inspection apparatus for inspecting for the presence of any pinholes, cracks, etc. in a can body.

REFERENCE SIGNS LIST 10 light source unit
10a upper side light source unit
10b lower side light source unit
11a, 11b transparent window
12 LED
15 light-detection unit
20 encoder
21 timing generation unit
22 LED drive circuit
23 peak hold/integrating circuit
24 judgment circuit 25 power supply
26 current monitoring unit
100 path of conveyance
W can body

The invention claimed is:

1. A can body inspection apparatus which comprises
a conveyance device which conveys a can body with an open end,
a light source which emits light to a can body which moves along the inside of a path of conveyance, and
a light detector which is arranged so as to face the open end face of the can body at a predetermined position inside the path of conveyance, which takes in the light which is leaked to the inside of the can body which is irradiated by the light from said light source, which is turned on through the open end face of the can body, and which outputs a detection signal which corresponds to the amount of light which is taken in and
which uses the detection signal from said light detector as the basis to inspect the can body,
said can body inspection apparatus comprising
light source controller for turning on said light source a predetermined number of times, the predetermined number of times being at least two times, at predetermined timings at which light can be taken in by said light detector through the open end face of the can body which is moving along the path of conveyance,
detection signal integrator for integrating signal values based on the detection signal which is output from said light detector due to on operations of said light source unit, and
condition judging device for judging condition of the can body based on an integrated value which is obtained by said detection signal integrator.

2. The can body inspection apparatus according to claim 1 wherein said detection signal integrates, as the signal values, peak level values of the detection signal which is output from said detector due to on operations of said light source.

3. The can body inspection apparatus according to claim 1 wherein said judging device judges the condition of the can body based on whether the integrated value which is obtained by said detection signal integrator is larger than a predetermined threshold value.

4. The can body inspection apparatus according to claim 1 wherein said light source controller turns said light source unit on at least at two timings of a timing right before a reference timing at which said open end face of the can body directly faces said light-detection unit and a timing right after the reference timing.

5. The can body inspection apparatus according to claim 4 wherein the time period between the reference timing and the timing right before when said light source is turned on and the time period from said reference timing to the timing right after when said light source is turned on are set the same.

6. The can body inspection apparatus according to claim 1 wherein said conveyance device conveys the can body without allowing it to rotate in an area at which light can be taken in by said light detector through the open end face of the moving can body.

7. The can body inspection apparatus according to claim 1 further comprising light source condition judging device for using the presence of a current which flows through said light source at a timing for supplying power from a power supply to turn on said light source as the basis to judge the condition of said light source.

8. A can body inspection method which uses a can body inspection apparatus which comprises
a conveyance device which conveys a can body with an open end,
a light source which emits light to a can body which moves along the inside of a path of conveyance, and
a light detector which is arranged so as to face the open end face of said can body at a predetermined position inside the path of conveyance, which takes in the light which is leaked to the inside of the can body which is irradiated by the light from said light source, which is turned on through the open end face of the can body, and which outputs a detection signal which corresponds to the amount of light which is taken in and
which uses the detection signal from said light detector as the basis to inspect said can body,
said can body inspection method comprising
a lighting step of turning on said light source a predetermined number of times, the predetermined number of times being at least two times, at predetermined timings at which light can be taken in by said light detector through the open end face of the can body which is moving along the path of conveyance,
a detection signal integrating step of integrating signal values based on the detection signal which is output from said light detector due to on operations of said light source, and
a condition judging step of judging condition of the can body based on an integrated value which is obtained by said detection signal integrating step.

9. The can body inspection method according to claim 8, wherein said detection signal integrating step integrates, as the signal values, peak level values of the detection signal which is output from said detector due to on operations of said light source.

10. The can body inspection apparatus according to claim 1, wherein the predetermined timings are dependent on the locations of the can along the path of conveyance.

11. The can body inspection apparatus according to claim 10, wherein the predetermined timings are dependent on the locations of the can along the path of conveyance defined by the rotation angles of the conveyance device.

12. The can body inspection apparatus according to claim 11, wherein the light source control turns on said light source to emit a first light emitting timing signal at a first position of the can at an upstream side relative to an origin position and a second light emitting timing signal at a second position of the can at a downstream side relative to the origin position along the path of conveyance, rotation angles of the first and second positions relative to the origin position being equidistant.

13. The can body inspection method according to claim 8, wherein the predetermined timings are dependent on the locations of the can along the path of conveyance.

14. The can body inspection method according to claim 13, wherein the predetermined timings are dependent on the locations of the can along the path of conveyance defined by the rotation angles of the conveyance device.

15. The can body inspection method according to claim 13, wherein the lighting step of turning on said light source turns on said light source to emit a first light emitting timing signal at a first position of the can at an upstream side relative to an origin position and a second light emitting timing signal at a second position of the can at a downstream side relative to the origin position along the path of conveyance, rotation angles of the first and second positions relative to the origin position being equidistant.

* * * * *